United States Patent
Bade et al.

(10) Patent No.: US 12,329,543 B1
(45) Date of Patent: Jun. 17, 2025

(54) APPARATUS AND METHOD FOR GENERATING A QUALITY DIAGNOSTIC OF ECG (ELECTROCARDIOGRAM) DATA

(71) Applicant: anumana, Inc., Cambridge, MA (US)

(72) Inventors: Sairam Bade, Suryapet (IN); Yash Mishra, Bangalore (IN); Shiva Verma, Bangalore (IN); Suthirth Vaidya, Bengaluru (IN); Shashi Kant, Bengaluru (IN); Ashim Prasad, Bangalore (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/599,435

(22) Filed: Mar. 8, 2024

(51) Int. Cl.
| | |
|---|---|
| A61B 5/00 | (2006.01) |
| A61B 5/346 | (2021.01) |
| G06V 10/00 | (2022.01) |
| G06V 30/10 | (2022.01) |
| G16H 30/40 | (2018.01) |
| G16H 50/20 | (2018.01) |

(52) U.S. Cl.
CPC ............ *A61B 5/7221* (2013.01); *A61B 5/346* (2021.01); *G06V 10/00* (2022.01); *G06V 30/10* (2022.01); *G16H 30/40* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 6,304,772 B1* | 10/2001 | Taha | A61B 5/7203 600/510 |
| 9,724,008 B2 | 8/2017 | Sullivan et al. | |
| 2013/0289424 A1* | 10/2013 | Brockway | A61B 5/6801 600/509 |
| 2016/0242664 A1 | 8/2016 | Wang et al. | |
| 2018/0116537 A1* | 5/2018 | Sullivan | A61N 1/046 |
| 2020/0160980 A1* | 5/2020 | Lyman | G06N 3/045 |
| 2021/0259778 A1* | 8/2021 | Newton | A61B 5/316 |

FOREIGN PATENT DOCUMENTS

| | | |
|---|---|---|
| CN | 113749668 A | 8/2022 |
| WO | 2023230345 A1 | 11/2023 |

* cited by examiner

*Primary Examiner* — Leon Viet Q Nguyen
(74) *Attorney, Agent, or Firm* — Caldwell Intellectual Property Law

(57) ABSTRACT

An apparatus and method for generating a quality diagnostic of analog ECG (electrocardiogram) data. The apparatus includes at least a processor and a memory communicatively connected to the at least a processor, wherein the memory contains instructions configuring the at least a processor to receive ECG data, extract a plurality of ECG parameters from the ECG data, convert the ECG data to one or more digitized ECG signals, validate the digitized ECG signals, wherein validating includes classifying the plurality of digitized ECG signals to a plurality of preliminary ECG parameters and determining an accuracy status of the extracted plurality of ECG parameters by comparing the plurality of preliminary ECG parameters to the extracted plurality of ECG parameters, and generate a quality diagnostic of the ECG data based on validation of the digitized ECG signals.

20 Claims, 8 Drawing Sheets

APPARATUS AND METHOD FOR GENERATING A QUALITY DIAGNOSTIC OF ECG (ELECTROCARDIOGRAM) DATA

FIELD OF THE INVENTION

The present invention generally relates to the field of electrocardiogram analysis. In particular, the present invention is directed to an apparatus and method for generating a quality diagnostic of ECG (electrocardiogram) data.

BACKGROUND

In many locales, patients never receive an electronic copy of ECG data. At best, they may receive printout of ECG data. As a result, diagnostic SaMDs (Software as a Medical Devices) can struggle to receive the direct digital output of an ECG device. Therefore, there is a need for a quality check method for an ECG printout to enable proper SaMD application functionality.

SUMMARY OF THE DISCLOSURE

In an aspect, an apparatus for generating a quality diagnostic of analog ECG (electrocardiogram) data. The apparatus includes at least a processor and a memory communicatively connected to the at least a processor, wherein the memory contains instructions configuring the at least a processor to receive ECG data, extract a plurality of ECG parameters from the ECG data, convert the ECG data to one or more digitized ECG signals, validate the digitized ECG signals, wherein validating includes classifying the plurality of digitized ECG signals to a plurality of preliminary ECG parameters and determining an accuracy status of the extracted plurality of ECG parameters by comparing the plurality of preliminary ECG parameters to the extracted plurality of ECG parameters, and generate a quality diagnostic of the ECG data based on validation of the digitized ECG signals.

In another aspect, a method for generating a quality diagnostic of analog ECG (electrocardiogram) data. The method includes using at least a processor configured receive ECG data, extract a plurality of ECG parameters from the ECG data, convert the ECG data to one or more digitized ECG signals, validate the digitized ECG signals, wherein validating includes classifying the plurality of digitized ECG signals to a plurality of preliminary ECG parameters and determining an accuracy status of the extracted plurality of ECG parameters by comparing the plurality of preliminary ECG parameters to the extracted plurality of ECG parameters, and generate a quality diagnostic of the ECG data based on validation of the digitized ECG signals.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to an apparatus and method for generating a quality diagnostic of analog ECG (electrocardiogram) data.

Aspects of the present disclosure can be used to implement a standardization and quality check method for an ECG printout image taken from a camera sensor in a mobile phone or other device. Such a standardization procedure may enable diagnostic and screening regulatory grade SaMDs to be developed for serving locales where the patient ECG is recorded and persisted only via a printout in a patient file and not as machine-readable digital data in an EHR (Electronic Health Record) system. Exemplary embodiments illustrating aspects of the present disclosure are described below in the context of several specific examples.

Aspects of the present disclosure can be used to give distinct audio or visual feedback to the physician to indicate when the ECG image does or does not meet the quality standards required for downstream diagnostic and screening SaMDs.

Figure 1:
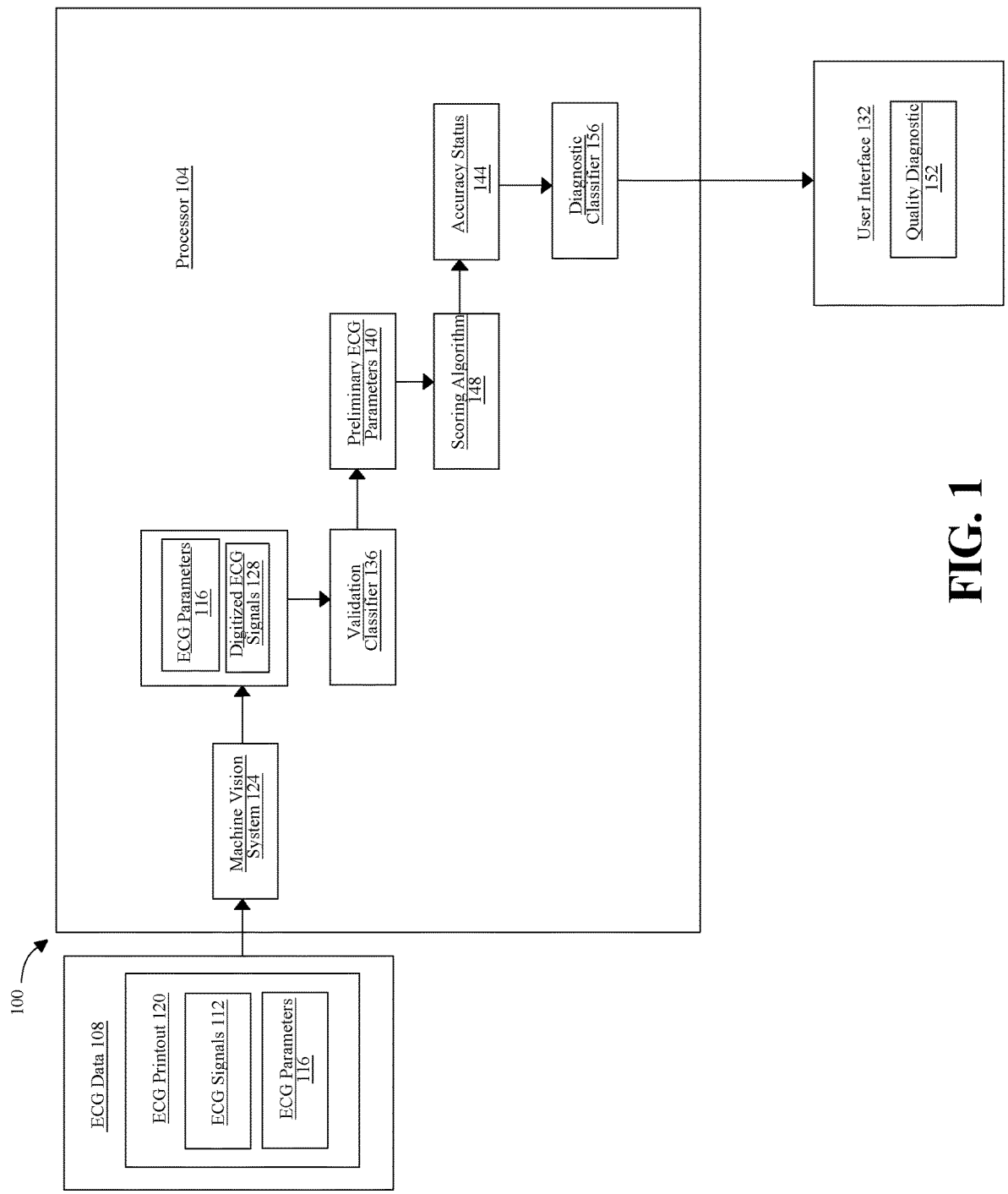
FIG. 1 is a block diagram of an exemplary embodiment of an apparatus for a quality diagnostic of analog ECG (electrocardiogram) data.

Referring now to FIG. 1, an exemplary embodiment of an apparatus 100 for generating a quality diagnostic of analog ECG (electrocardiogram) data is illustrated. Apparatus 100 includes a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus 100 includes a memory. Memory is communicatively connected to processor 104. Memory may contain instructions configuring processor 104 to perform tasks disclosed in this disclosure. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, apparatus, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example, and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, without limitation, via a bus or other facility for intercommunication between elements of a computing device. Communicative connecting may also include indirect connections via, for example, and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may be configured to receive ECG (electrocardiogram) data 108. ECG data may include digital ECG data and/or analog ECG data. As used in the current disclosure, "digital ECG data" refers to the digital representation of the electrical activity of the heart recorded over time. As used in the current disclosure, "analog ECG data" refers to an analog representation of the electrical activity of the heart recorded over time. ECG data 108 may include a plurality of ECG signals 112 represented in a digital or analog format. As used in the current disclosure, a "format" refers to a method of representing information or data using continuous and continuously variable physical quantities, such as electrical voltage. Electrical activity may be depicted using electrocardiogram (ECG) signals. As used in the current disclosure, a "electrocardiogram signal" is a signal representative of electrical activity of heart. The ECG signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The ECG signal can help diagnose various heart conditions, such as arrhythmias, myocardial infarction (heart attack), conduction abnormalities, and electrolyte imbalances.

Still referring to FIG. 1, ECG data 108 may refer to the digital methods of recording and storing ECG signals 112 in a digital format. This may include formats such as DICOM, HL7, or simple text-based formats. These files contain the time and voltage measurements, patient information, and metadata. In an embodiment, digital ECG data may be received from a database, application program interface (API), electronic health records, and the like. As used in the current disclosure, "electronic health records" are digital records containing a patient's medical history, diagnoses, medications, treatment plans, and other relevant information. EHRs are used by healthcare providers to track and manage patient care. In an embodiment, digital ECG data may include a plurality of metadata. As used in the current disclosure, "metadata" refers to descriptive or informational data that provides details about the digital ECG data. Metadata may include descriptive metadata, wherein descriptive metadata is configured to describe the content, context, and structure of the data. In an embodiment, metadata may include data regarding the lead system the digital ECG data was recording. ECGs are typically recorded using multiple leads, each of which provides a different view of the heart's electrical activity. Common lead systems include the 12-lead, 6-lead, 3-lead, and single-lead ECGs. The specific lead system used to generate the digital ECG data and their configurations may be documented in the metadata. In some embodiments, metadata associated with the digital ECG data may include information such as time, geographic location, medical facility names, medical professional logs, patient names, patient IDs, patient data, along with any other patient specific data. Metadata may be used to describe records of how the data has been accessed, utilized, or modified over time, aiding in understanding data usage patterns, and optimizing access.

Still referring to FIG. 1, ECG data 108 may refer to the traditional methods of recording and storing ECG signals 112 in an analog, non-digital format. ECG data 108 involves the use of paper or other analog recording mediums to graphically represent the electrical activity of the heart. In some embodiments, the analog electrical signals from the heart are recorded directly onto special ECG paper. This paper typically has a grid pattern with horizontal and vertical lines, which helps in measuring the time and voltage of the ECG waveforms. ECG data 108 also may use electrodes placed on the patient's skin. The electrodes may be connected to leads that transmit the electrical signals to the recording device. Different lead configurations may be used, such as the 12-lead system, 6-lead system, 3-lead system, etc., each providing a different perspective of the heart's electrical activity. ECG data 108 may reflect electrical activity of the heart is continuously recorded as a series of analog waveforms on the ECG paper. The most important components of these waveforms include the P-wave, QRS complex, and T-wave, which represent different phases of the cardiac cycle.

With continued reference to FIG. 1, ECG data 108 may be recorded and stored on various physical mediums. ECG data 108 may be stored on ECG paper. ECG machines printed the electrical waveforms directly onto a roll or sheets of special ECG paper. The resulting ECG tracings were a graphical representation of the heart's electrical activity over time. These paper printouts were often physically archived in patient medical records. ECG data 108 could also be recorded and stored on magnetic tape. Specialized magnetic tape recorders may be used to capture the analog signal, which could then be played back for analysis. This medium allowed for easier archiving and retrieval compared to paper. In some cases, ECG data 108 may be recorded onto analog audio cassette tapes. While primarily designed for audio, these tapes could be adapted for ECG signal storage, especially in ambulatory monitoring systems. The signal could be played back and analyzed using dedicated equipment. ECG data 108 could be stored on photographic film, similar to how images are stored on film. These films used light exposure to capture the ECG waveforms and could be processed and printed for analysis or archiving. In a few cases, ECG data 108 may be stored on analog magnetic disk drives, similar to early computer storage systems. These systems were less common for ECG signal storage but were used in some research or specialized applications.

Still referring to FIG. 1, ECG data 108 may include an ECG printout 120. An "ECG printout," as used herein, is a graphical representation of the electrical activity of the heart recorded over a period of time. An ECG printout 120 may be generated by an ECG machine, which measures the electrical impulses generated by the heart during each heartbeat. ECG printout 120 may be generated by an analog ECG machine. Analog ECG machines may capture and display the electrical signals generated by the heart in an analog format. Analog ECG machines may produce a paper printout, such as ECG printout 120, of the ECG recording, with the waveforms graphically illustrated on the paper. ECG printout 120 may be generated by a digital ECG machine. Digital ECG machines may convert the analog electrical signals from the heart into digital data for processing and analysis. Digital ECG machines may provide electronic outputs in the form of digital files, allowing for easy storage, transmission, and analysis. Digital ECG machines may provide outputs in the form paper printout, such as ECG printout 120, of the processing and analysis. ECG printout 120 may provide valuable information about the heart's rhythm, rate, and various other parameters. The ECG printout 120 may indicate a specific combination of electrodes used to record the electrical signals from the heart. The ECG printout 120 may indicate details such as patient name, date, time, and often age and sex. The ECG printout 120 may indicate a baseline, which is the reference line from which the electrical activity of the heart is measured. The ECG printout 120 may include a grid and calibration markers indicating the duration and amplitude of the recorded signals. The ECG printout 120 may include waveforms as described above. The ECG printout 120 may include annotations or labels indicating specific events or abnormalities detected during the recording. The ECG printout 120 may include axis measurements, representing the average direction of electrical activity in the heart. The ECG printout 120 may include a plurality of ECG parameters 116. "ECG parameters," as used herein, are measurements and characteristics derived from the electrical activity of the heart as recorded by an ECG machine. ECG parameter may include measurements and characteristics derived from ECG signals 112 as described above. ECG parameter may be represented as name-value pairs, providing information about various aspects of the cardiac cycle. Name-value pairs may include ventricular rate, QT interval, QTc calculation, QRS duration, P-R interval, P axis, R axis, T axis, and the like.

Still referring to FIG. 1, apparatus 100 may include at least a camera configured to capture an image of ECG data 108 for processor 104 to analyze. As used in this disclosure, a "camera" is a device that is configured to sense electromagnetic radiation, such as without limitation visible light, and generate an image representing the electromagnetic radiation. In some cases, a camera may include one or more optics. Exemplary non-limiting optics include spherical lenses, aspherical lenses, reflectors, polarizers, filters, windows, aperture stops, and the like. In some cases, at least a camera may include an image sensor. Exemplary non-limiting image sensors include digital image sensors, such as without limitation charge-coupled device (CCD) sensors and complimentary metal-oxide-semiconductor (CMOS) sensors, chemical image sensors, and analog image sensors, such as without limitation film. In some cases, a camera may be sensitive within a non-visible range of electromagnetic radiation, such as without limitation infrared. As used in this disclosure, "image data" is information representing at least a physical scene, space, and/or object. In some cases, image data may be generated by a camera. "Image data" may be used interchangeably through this disclosure with "image," where image is used as a noun. An image may be optical, such as without limitation where at least an optic is used to generate an image of an object. An image may be material, such as without limitation when film is used to capture an image. An image may be digital, such as without limitation when represented as a bitmap. Alternatively, an image may be comprised of any media capable of representing a physical scene, space, and/or object. Alternatively, where "image" is used as a verb, in this disclosure, it refers to generation and/or formation of an image.

Still referring to FIG. 1, in some embodiments, apparatus 100 may include a machine vision system 124 that includes the camera. A machine vision system 124 may use images from at least a camera, to make a determination about a scene, space, and/or object. For example, in some cases a machine vision system 124 may be used for world modeling or registration of objects within a space. In some cases, registration may include image processing, such as without limitation object recognition, feature detection, edge/corner detection, and the like. Non-limiting examples of feature detection may include scale invariant feature transform (SIFT), Canny edge detection, Shi Tomasi corner detection, and the like. In some cases, registration may include one or more transformations to orient a camera frame (or an image or video stream) relative a three-dimensional coordinate system; exemplary transformations include without limitation homography transforms and affine transforms. In an embodiment, registration of first frame to a coordinate system may be verified and/or corrected using object identification and/or computer vision, as described above. For instance, and without limitation, an initial registration to two dimensions, represented for instance as registration to the x and y coordinates, may be performed using a two-dimensional projection of points in three dimensions onto a first frame, however. A third dimension of registration, representing depth and/or a z axis, may be detected by comparison of two frames; for instance, where first frame includes a pair of frames captured using a pair of cameras (e.g., stereoscopic camera also referred to in this disclosure as stereo-camera), image recognition and/or edge detection software may be used to detect a pair of stereoscopic views of images of an object; two stereoscopic views may be compared to derive z-axis values of points on object permitting, for instance, derivation of further z-axis points within and/or around the object using interpolation. This may be repeated with multiple objects in field of view, including without limitation environmental features of interest identified by object classifier and/or indicated by an operator. In an embodiment, x and y axes may be chosen to span a plane common to two cameras used for stereoscopic image capturing and/or an xy plane of a first frame; a result, x and y translational components and ϕ may be pre-populated in translational and rotational matrices, for affine transformation of coordinates of object, also as described above. Initial x and y coordinates and/or guesses at transformational matrices may alternatively or additionally be performed between first frame and second frame, as described above. For each point of a plurality of points on object and/or edge and/or edges of object as described above, x and y coordinates of a first stereoscopic frame may be populated, with an initial estimate of z coordinates based, for instance, on assumptions about object, such as an assumption that ground is substantially parallel to an xy plane as selected above. Z coordinates, and/or x, y, and z coordinates, registered using image capturing and/or object identification processes as described above may then be compared to coordinates predicted using initial guess at transformation matrices; an error function may be computed using by comparing the two sets of points, and new x, y, and/or z coordinates, may be iteratively estimated and compared until the error function drops below a threshold level. In some cases, a machine vision system 124 may use a classifier, such as any classifier described throughout this disclosure.

Still referring to FIG. 1, machine vision system 124 may include optical character recognition (OCR) techniques such as an OCR reader. OCR is a technology that extracts text and characters from images or scanned documents and converts it into machine-readable text. In some cases, recognition of at least a keyword from an image component may include one or more processes, including without limitation optical character recognition (OCR), optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of the image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted features can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. The second pass may include adaptive recognition and use letter shapes recognized with high confidence on a first pass to recognize better remaining letters on the second pass. In some cases, a two-pass approach may be advantageous for unusual fonts or low-quality image components where visual verbal content may be distorted. Another exemplary OCR software tool includes OCRopus. OCRopus development is led by German Research Centre for Artificial Intelligence in Kaiserslautern, Germany. In some cases, OCR software may employ neural networks, for example neural networks.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

Still referring to FIG. 1, processor 104 is configured to extract a plurality of ECG parameters 116 from ECG data 108. Processor 104 may use the OCR reader or other components of the machine vision system 124 to extract the ECG parameters 116, ECG signals 112, graphical representations, and other aspects of image data related to ECG data 108.

Still referring to FIG. 1, the processor is configured to process an image of ECG data 108. An image may include the ECG printout 120 as described above. Processing an image may use the machine visions system as described above. Processing the ECG printout 120 may include converting image data, such as depicted ECG signals 112, to digitized ECG signals 128. A "digital ECG signal," as used herein is electrocardiogram data represented as a series of discrete voltage values, such as for example, in the form of an array or sequence of numbers. The voltage values may correspond to the electrical activity of the heart, such as the changes in voltage associated with the depolarization and repolarization of cardiac muscle during each heartbeat. The sequence of voltage values in the array may correspond to different time points, allowing the representation of the ECG signal in the time domain. Each value in the array may correspond to a specific moment during the cardiac cycle.

Still referring to FIG. 1, converting image data to digitized ECG signals 128 may include preprocessing the ECG printout 120 to enhance the image quality. Preprocessing may include converting the color image to grayscale, adjusting contrast and brightness, cropping or resizing the image, applying filters (e.g., Gaussian, median) to reduce noise and the like. Processing the ECG printout 120 may include performing thresholding or edge detection, to separate the ECG signals 112 from the background and grid lines. Using edge detection algorithms (e.g., Sobel, Canny) or morphological operations (e.g., dilation, erosion) may emphasize the boundaries of the ECG signals 112, isolate the ECG waveform from the rest of the image, and extract the region of interest containing the ECG waveform. Processing the ECG printout 120 may include using peak detection algorithms or signal processing techniques to identify significant points, such as identifying R-peaks within a QRS complex. Peak detection algorithms may include threshold-based methods wherein a threshold value determines which peaks are identified. Peaks exceeding this threshold may be considered significant. Processing the ECG printout 120 may include.

Still referring to FIG. 1, processor 104, as function of one more of the processing steps described above, may convert the visual representations of the ECG signals 112 into a digital format. For example, the ECG waveform in an ECG printout 120 may be depicted in a grayscale image where the intensity of each pixel corresponds to the amplitude of the signal at that point in time. The vertical axis of the ECG waveform may correspond to the amplitude of the signal. Each pixel along this axis may have a specific intensity value. Processor 104 may map the pixel intensity values along the vertical axis of the ECG waveform to voltage values and assign digital values to represent the voltage levels of the ECG signals 112 at each point in time. By mapping these pixel intensity values along the vertical axis, a connection between the visual representation and the actual voltage values of the ECG signals 112 may be formed. After mapping, processor 104 may assign digital values to represent the amplitude of the ECG signals 112 at each point in time. The digital values may be numerical and may be represented in a binary format. The range of digital values may be determined by factors such as the bit depth of the digital representation. For example, in an 8-bit system, each pixel's intensity value may be converted to a digital value ranging from 0 to 255. This digital format may be a representation of the voltage level at that specific point in the ECG waveform.

Still referring to FIG. 1, after determining the digital format, processor 104 may determine a temporal relationship between sampled points. A "sampled point" refers to a measurement of the electrical activity of the heart at a specific point in time. Processor 104 may be configured to determine the time duration covered by each pixel column or row in the digital representation/format. If the image was captured at a specific rate, this information may be used to calculate the time duration between pixels. For example, calibration marks or information on the printout indicating the time duration may be represented by a certain length or number of pixels on the ECG printout 120. Processor 104 may be configured to recognize these calibration marks and use them to establish a relationship between the physical dimensions on the printout and the corresponding time duration. In another embodiment, the ECG printout 120 may include textual information indicating the paper speed or time intervals. Processor 104 may use OCR algorithms to extract and interpret this information, wherein the OCR is trained to recognize specific patterns or keywords related to temporal scaling. The temporal relationship between sampled points may ensure that the digital representation/format accurately reflects the timing of the original ECG signals 112.

Still referring to FIG. 1, based on the mapping and temporal durations steps described above, processor 104 may organize the digital representations/formats into an array structure to generate digitized ECG signals 128. The array may be one-dimensional or two-dimensional depending on the ECG data. In embodiments where the ECG data is one-dimensional, the array may have a single row or column where each element corresponds to the voltage value at a specific moment in time. In embodiments where the ECG data is two-dimensional, the array may have rows and columns, where each row represents a specific moment in time, and each column represents a spatial position along the ECG waveform. Each row or column in the array represents a specific moment in time, and the values in that row or column represent the amplitude of the ECG signal at that time. The digital ECG may be in a machine-readable formation for further integration into software programs and analysis. For example, formats may include CSV (Comma-Separated Values) where each row represents a time point, and columns represent different parameters or features, including time and voltage. Other examples of formats may include JSON (JavaScript Object Notation), HDF5 (Hierarchical Data Format version 5), DICOM (Digital Imaging and Communications in Medicine), and the like.

Still referring to FIG. 1, the processor 104 is configured to validate a plurality ECG signals 112 and/or digitized ECG signals 128. For example, validating may include assessing the quality of ECG data 108, such as the ECG printout 120, as the accuracy of ECG signals so obtained depends on the quality of the image captured from the ECG machine. Assessing the quality of the ECG printout 120 may include verifying the extracted ECG parameters 116 against plurality ECG signals 112 and the like to verify that plurality ECG signals 112 derive the same ECG parameters extracted. In some embodiments, validating the ECG data 108 may include receiving a user input to verify the accuracy of digital ECG signal. For example, processor 104 may be communicatively connected to a user interface 132, wherein the digital ECG may be transmitted and displayed, and processor 104 may receive user input. A "user interface," as used herein, is a means by which a user and a computer system interact; for example, through the use of input devices and software. A user interface 132 may include a graphical user interface 132 (GUI), command line interface (CLI), menu-driven user interface, touch user interface, voice user interface (VUI), form-based user interface, any combination thereof, and the like. A user interface 132 may include a smartphone, smart tablet, desktop, or laptop operated by the user. In an embodiment, the user interface 132 may include a graphical user interface. A "graphical user interface (GUI)," as used herein, is a graphical form of user interface that allows users to interact with electronic devices. In some embodiments, GUI may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pulldown menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access. Information contained in user interface 132 may be directly influenced using graphical control elements such as widgets. A "widget," as used herein, is a user control element that allows a user to control and change the appearance of elements in the user interface 132. In this context a widget may refer to a generic GUI element such as a check box, button, or scroll bar to an instance of that element, or to a customized collection of such elements used for a specific function or application (such as a dialog box for users to customize their computer screen appearances). User interface 132 controls may include software components that a user interacts with through direct manipulation to read or edit information displayed through user interface 132. Widgets may be used to display lists of related items, navigate the system using links, tabs, and manipulate data using check boxes, radio boxes, and the like.

Still referring to FIG. 1, validating plurality of digitized ECG signals 128 may include using a machine learning model, such as a validation classifier 136. A validation classifier 136 may be configured to receive plurality of digitized ECG signals 128 as an input and output a plurality of preliminary ECG parameters 140. Preliminary ECG parameters 140 refer to parameters derived from digitized ECG signals by a computing device. Validation classifier 136 training data may include a plurality of digitized ECG signals 128 correlated to a plurality of textbook validators of ECG parameters 116. Textbook validators of ECG parameters 116 may refer to a plurality of standard ECG parameters 116 definition, identifiers, notable characteristics, formulas, and the like. For example, textbook validators of ECG parameters 116 may include formulas and algorithms for deriving ECG parameters 116. In this case, validation classifier 136, based on the inputted digitized ECG signal, may output the correlating formula for calculating the related ECG parameter, wherein processor 104 may perform the calculation to verify if the preliminary ECG matches or is close to the ECG parameter. For example, the ECG parameters 116 from the ECG print out may be a heart rate BPM, validation classifier 136 may match a formula for determining a heart rate BPM based on plurality digitized ECG signals input wherein processor 104 may compute the classified formula and output the preliminary ECG parameter for the heart rate. Validators of ECG parameters 116 may include identifiers/standardized labels or symbols used to represent specific features or measurements derived from an ECG waveform. Validators of ECG parameters 116 may include a plurality of sample arrays of voltage values (digitized ECG signals) correlated to ECG parameters 116.

Still referring to FIG. 1, processor 104 may be configured to compare and score the preliminary ECG parameter to the OCR extracted ECG parameter and determine an accuracy status 144. Processor 104 may use a scoring algorithm 148 implementing a threshold to determine the accuracy status 144 of preliminary ECG parameter. A "scoring algorithm," as used herein, is a set of rules or procedures designed to evaluate, quantify, or rank entities based on a criteria. A criterion may include a threshold as described below. Examples of scoring algorithms may include linear scoring, logistic regression, decision trees, random forest algorithm, and the like. An "accuracy status," as used herein, is a variable classifying the accuracy of preliminary ECG parameter. For example, the accuracy status 144 may be a linguistic or numerical variable. An accuracy status 144 may include a pass or fail status, wherein a threshold is used to determine the status of the preliminary ECG parameter. The threshold may include numerical ranges preliminary ECG parameters 140 may be in in proximity to the OCR extracted ECG Parameter to label the preliminary ECG parameter with a pass status. For example, the threshold may determine the primary may only be 0.5% off (greater or lesser) from the OCR extracted ECG parameter to be validated with a pass status. In some embodiments, the threshold may be determined by a user input received through user interface 132 as described above. In some cases, data from the ECG printout 120 may indicate that the extracted ECG parameter may be flexible, for example, being estimated because of indicators such as annotations or labels on the printout indicating specific events or abnormalities detected during the recording. For example, specific events or abnormalities may include arrhythmias, ischemia, electrolyte imbalances, drug effects, patient movement, other specific physiological or physical characteristics about a patient/user being recorded, and the like. In this case, the threshold may be determined using a threshold classifier to determine a threshold based on specific events or abnormality that defines acceptable margin of error or tolerance in a preliminary ECG parameter based on the ECG data 108. Threshold classifier training data may include data correlating a plurality of annotations or labels indicating specific events or abnormalities to a plurality of thresholds.

Still referring to FIG. 1, plurality ECG signals 112 and/or ECG parameters 116 may be validated or invalidated based on the accuracy status 144 of the preliminary ECG parameters 140. Validation of such parameters may indicate the quality of the ECG printout 120 for SaMDs (Software as a Medical Device) integration. SaMDs may provide automated analysis of ECG data, helping to detect and interpret abnormalities. This may include identifying arrhythmias, ST-segment changes, and other indicators of cardiac conditions. The quality and resolution of an ECG printout 120 can significantly impact the performance and accuracy of Software as a Medical Device (SaMD) used for ECG analysis. Higher-quality ECG printouts with better resolution provide more detailed and accurate information about a person's cardiac activity. Lower-quality ECG printouts may contain more signal noise and artifacts. These could be due to poor electrode contact, patient movement, or other factors. SaMDs designed for ECG analysis need to be robust enough to handle and, if possible, mitigate the impact of such noise to avoid false positives or negatives in their assessments. Therefore, processor 104 is configured to generate a quality diagnostic of ECG data 108 based on the validated or invalidated data. In some cases, the accuracy score may be calculated for the overall average quality/accuracy of ECG signals 112 or ECG data 108. The threshold classifier training data may include threshold parameters for determining the average accuracy score.

Still referring to FIG. 1, a "quality diagnostic," as used herein, is a representation of the quality of ECG data 108. For example, a quality diagnostic 152 may regard the quality of the ECG printout 120. Quality diagnostic 152 may include an auditory representation such an auditory, message alert, or notification transmitted through the user interface 132. An auditory representation may include sounds to indicate a pass status or a fail status regarding the overall quality of the ECG printout 120. Quality diagnostic 152 may include a visual representation, displayed through the user interface 132, regarding the quality status of the ECG printout 120. The visual representation may include a report or assessment detailing the accuracy score for each ECG signal and the like of ECG data 108. The visual representation may include information describing the clarity and fidelity of the ECG signals 112, such as the presence of noise or interference, signal artifacts, such as baseline wander or electrical interference, and the like. The visual representation may include information describing the alignment of the ECG waveforms within the grid, as poor alignment hinders accurate measurement of intervals and durations. The visual representation may include information describing an incomplete assessment, such as an inadequate duration of the recording for comprehensive analysis. The visual representation may include information recognizing and labeling artifacts caused by patient movement or other external factors. Data derived from image processing techniques and other algorithms as disclosed above may be used to generate the quality diagnostic 152. In some embodiments, a machine learning model, such as a diagnostic classifier 156, may be used to classify ECG data 108, such as the ECG printout 120 to one or more flags. A "flag," used herein, is a label indicating an issue with ECG data 108. A flag may be information detailed in a visual representation as described above, such as patient movement, unclear ECG signal, presence of noise and the like. The diagnostic classifier training data may include data correlating ECG data 108, such an ECG printout 120, to a plurality of flags.

Still referring to FIG. 1, machine learning models as described herein may be validated. For example, processor 104 may use methods such as generating an electrocardiogram verification to validate the output of a machine learning model as described in Nonprovisional application Ser. No. 18/403,840 filed on Jan. 30, 2024, and entitled "APPARATUS AND METHOD FOR GENERATING AN ELEC- TROCARDIOGRAM VERIFICATION SET," the entirety of which is incorporated herein by reference.

Still referring to FIG. 1, machine learning models as described herein improve the performance power of processor 104 my optimizing processor 104 functionality. Machine learning models can be effectively trained on extensive and diverse datasets, encompassing individuals from various ethnicities, to understand intricate patterns and variations in ECG signals 112. This approach enhances the model's ability to identify parameters accurately and consistently, thereby minimizing the risk of human interpretation errors. For example, validation classifier 136 may be trained on an extensive and diverse dataset, ensuring that it can accommodate the subtle differences in ECG characteristics among individuals of different ethnic backgrounds. This inclusive training approach may empower processor 104 to interpret ECG signals 112 from ECG printout 120 and determine preliminary ECG parameters 140 with greater accuracy and adaptability to the diverse characteristics present in real-world scenarios. Without the implementation of a machine-learning model, there would be a trade in the performance power of processor 104, such as time and accuracy, in order to sort the data and generate preliminary ECG parameters 140 that play a critical role in validating analog ECG data as described above. The ability to continuously train a machine-learning model cable of learning to identify new trends or correlations within a fluctuating quantity of data is a benefit that would not be realized otherwise, without the tradeoff in performance efficiency.

Still referring to FIG. 1, machine learning models as described herein improve the performance power of processor 104 by optimizing processor 104 functionality. For example, machine learning models can be effectively trained on extensive and diverse datasets, additionally encompassing individuals from various ethnicities, to understand intricate patterns and variations in ECG signals 112. This approach enhances the model's ability to identify parameters accurately and consistently, thereby minimizing the risk of human interpretation errors. For example, validation classifier 136 may be trained on an extensive and diverse dataset, ensuring that it can accommodate the subtle differences in ECG characteristics among individuals of different ethnic backgrounds. This inclusive training approach may empower processor 104 to interpret ECG signals 112 from ECG printout 120 and determine preliminary ECG parameters 140 with greater accuracy and adaptability to the diverse characteristics present in real-world scenarios. Without the implementation of a machine-learning model, there would be a trade in the performance power of processor 104, such as time and accuracy, in order to sort the data and generate preliminary ECG parameters 140 that play a critical role in validating analog ECE data as described above. The ability to continuously train a machine-learning model cable of learning to identify new trends or correlations within a fluctuating quantity of data is a benefit that would not be realized otherwise, without the tradeoff in performance efficiency.

Figure 2:
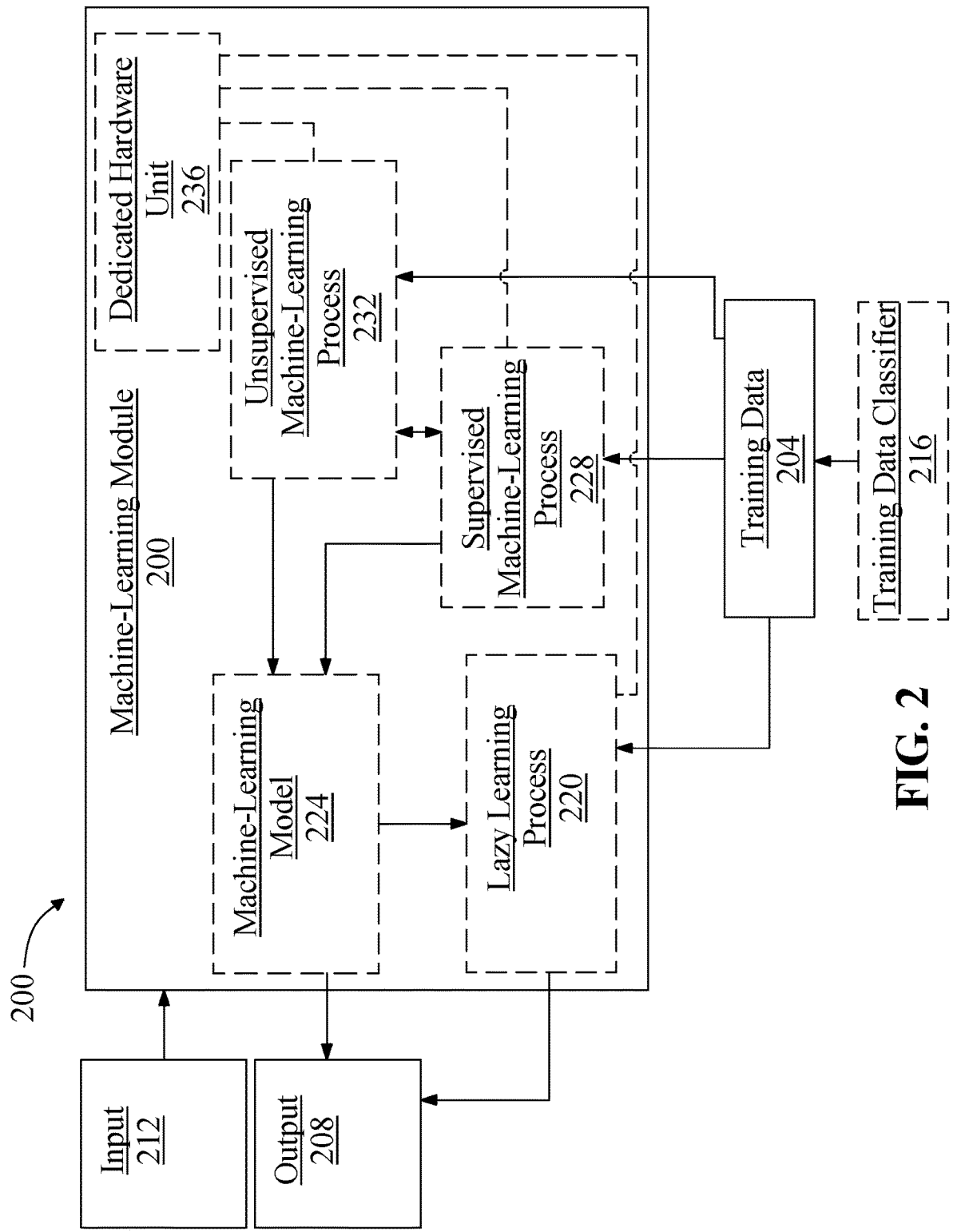
FIG. 2 is a block diagram of an exemplary machine-learning process.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 204 to generate an algorithm instantiated in hardware or software logic, data structures, and/or functions that will be performed by a computing device/module to produce outputs 208 given data provided as inputs 212; this is in contrast to a non-machine learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively, or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to [something that characterizes a subpopulation, such as a cohort of persons and/or other analyzed items and/or phenomena for which a subset of training data may be selected].

Still referring to FIG. 2, computing device 204 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A) \div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 204 may then calculate a likelihood table by calculating probabilities of different data entries and classification labels. Computing device 204 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 2, computing device 204 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 2, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 2, training examples for use as training data may be selected from a population of potential examples according to cohorts relevant to an analytical problem to be solved, a classification task, or the like. Alternatively, or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively, or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 2, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 2, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively, or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 2, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 2, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 2, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 2, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 2, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max} : X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 2, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described in this disclosure as inputs, outputs as described in this disclosure as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

With further reference to FIG. 2, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 2, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 2, machine learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 232 may not require a response variable; unsupervised processes 232 may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 2, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 2, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 2, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 2, one or more processes or algorithms described above may be performed by at least a dedicated hardware unit 236. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 236 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 236 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 236 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 3:
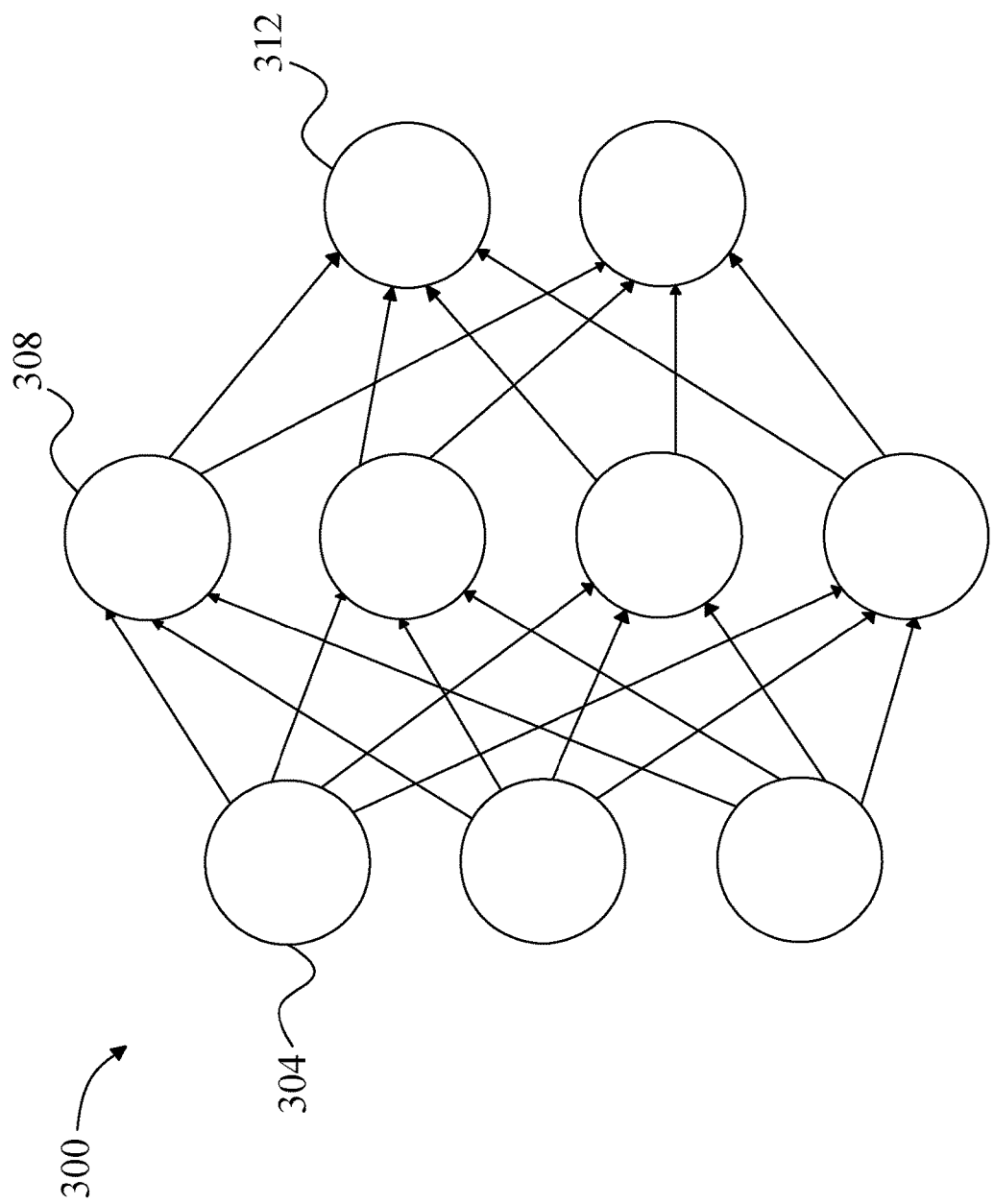
FIG. 3 is a diagram of an exemplary embodiment of a neural network.

Referring now to FIG. 3, an exemplary embodiment of neural network 300 is illustrated. A neural network 300 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 304, one or more intermediate layers 308, and an output layer of nodes 312. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 4:
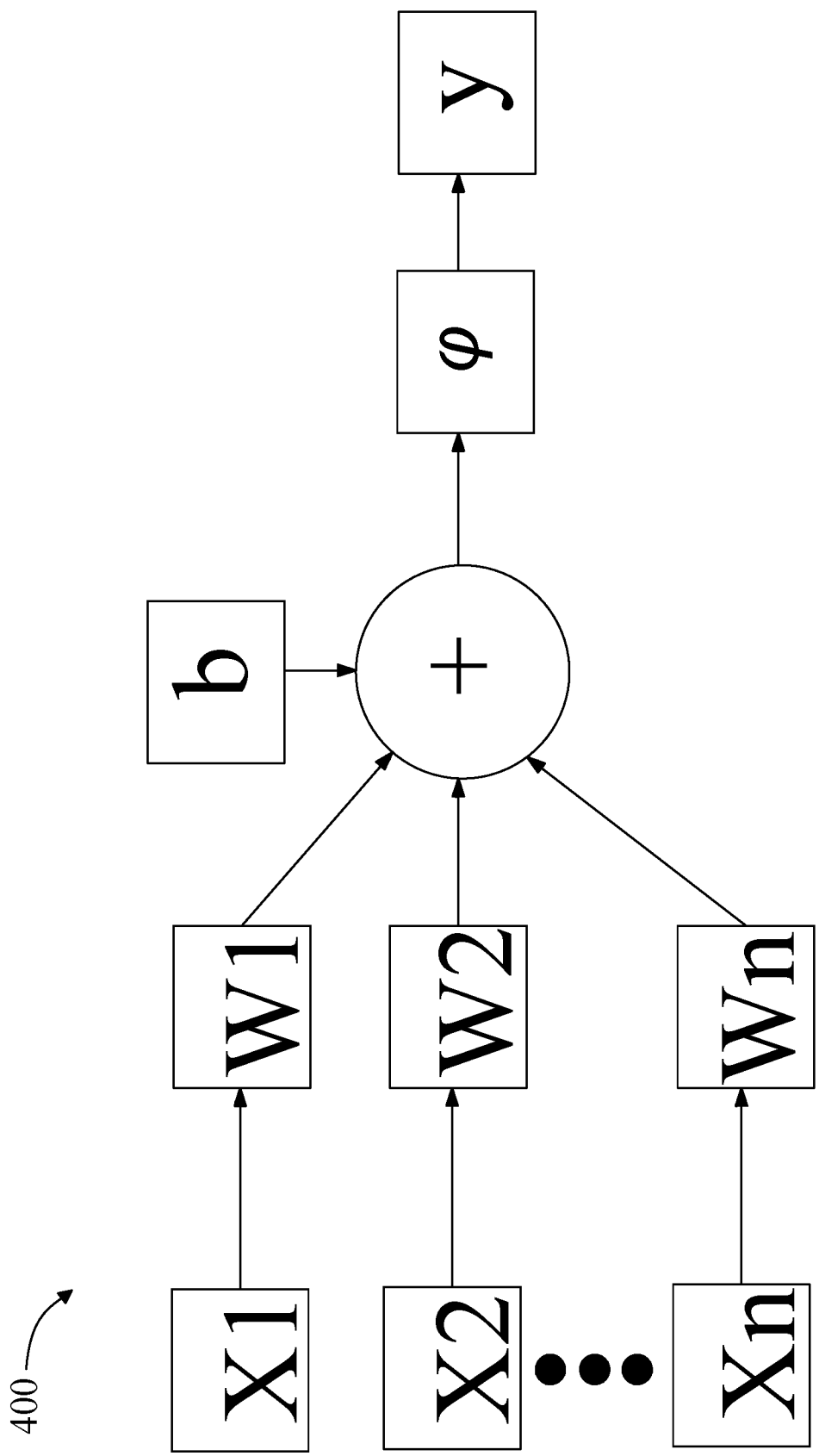
FIG. 4 is a diagram of an exemplary embodiment of a node of a neural network.

Referring now to FIG. 4, an exemplary embodiment of a node 400 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 5:
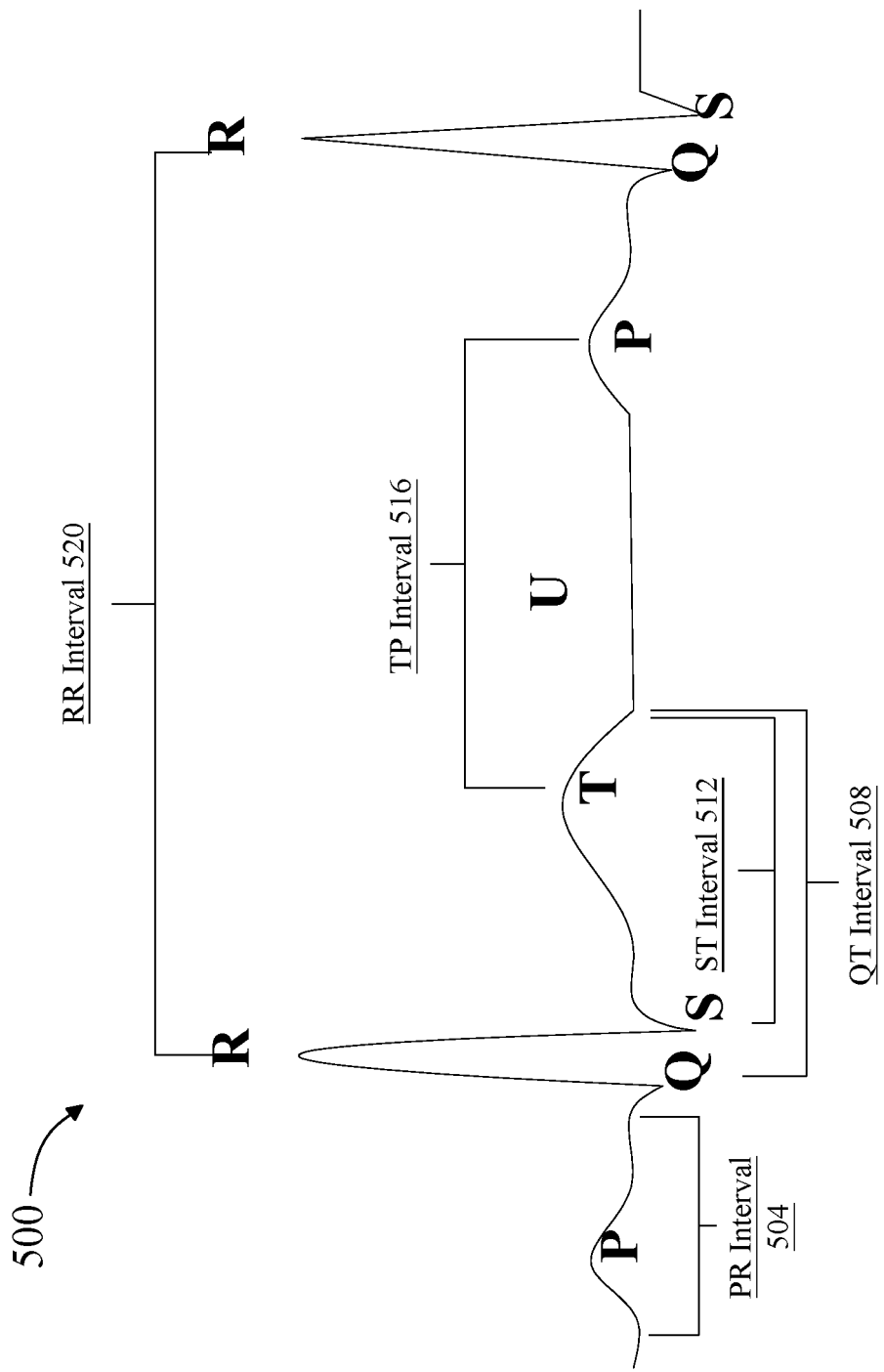
FIG. 5, is a diagram of an ECG reading with annotations.

Referring now to FIG. 5, a diagram of an ECG diagram 500 is illustrated. ECG diagram 500 may be depicted in an ECG printout as described above. ECG diagram 500 may include a plurality of parameters such a PR interval 504, QT interval 508. ST interval 512, TP interval 516, RR interval 520, and the like. The P-wave may reflect atrial depolarization (activation). The PR interval 504 is the distance between the onset of the P-wave to the onset of the QRS complex. The PR interval 504 may be assessed to determine whether impulse conduction from the atria to the ventricles is normal. PR interval 504 may be measured in seconds, for example, $$\text{heart rate} = \frac{60}{PR \text{ Interval}} \text{ (in seconds)}.$$

The QT interval 508 may reflect the total duration of ventricular depolarization and repolarization. It may be measured from the onset of a QRS complex to the end of the T-wave. The QT duration may be inversely related to heart rate; i.e. the QT interval 508 may increase at slower heart rates and decrease at higher heart rates. Therefore, to determine whether the QT interval 508 is within normal limits, it may be necessary to adjust for the heart rate. The heart rate-adjusted QT interval 508 is referred to as the corrected QT interval 508 (QTc interval). A long QTc interval may indicate increased risk of ventricular arrhythmias. The QTc interval may be in the range of 0.36 to 0.44 seconds.

$$QT_c = \frac{QT_{interval}}{\sqrt{RR_{interval}}} \text{ (measured in seconds)},$$

where RR interval 520 is the time between two consecutive R waves. The QRS complex may represent the depolarization (activation) of the ventricles which may be depicted between the Q-, R- and S-wave, although it may not always display all three waves. Since the electrical vector generated by the left ventricle is usually many times larger than the vector generated by the right ventricle, the QRS complex is a reflection of left ventricular depolarization.

Still referring to FIG. 5, the ST interval 512 is the segment on the ECG that starts at the end of the QRS complex and extends to the beginning of the T wave. It represents the early part of ventricular repolarization. The ST segment may be relatively isoelectric, meaning it is at the baseline, with minimal elevation or depression. The normal duration of the ST interval 512 is usually around 0.12 seconds (120 milliseconds). The TP interval 516 is the segment on the ECG that extends from the end of the T wave to the beginning of the next P wave. It represents the time when the ventricles are fully repolarized and are in a resting state. The duration of the TP interval 516 may be variable but is typically short, as it may represent the brief pause between cardiac cycles. Significant deviations may be associated with certain conditions affecting repolarization. The RR interval 520 is the time between two consecutive R waves on the ECG. It may represent the duration of one cardiac cycle, encompassing both atrial and ventricular depolarization and repolarization. The RR interval 520 may be measured in seconds and can be used to calculate heart rate (beats per minute) using a formula, such as $$\text{heart rate} = \frac{60}{PR \text{ Interval}} \text{ (in seconds)}.$$

The intervals described above may be used to determine a ventricular rate which refers to the number of ventricular contractions (heartbeats) that occur in one minute. It may be closely related to the RR interval 520 on an electrocardiogram (ECG), as the RR interval 520 represents the time between two consecutive ventricular contractions. The formula for calculating the ventricular rate (heart rate) in beats per minute (bpm) may be:

$$\text{Ventricular rate} = \frac{60}{RR \text{ Interval}} \text{ (in seconds)}.$$

Figure 6:
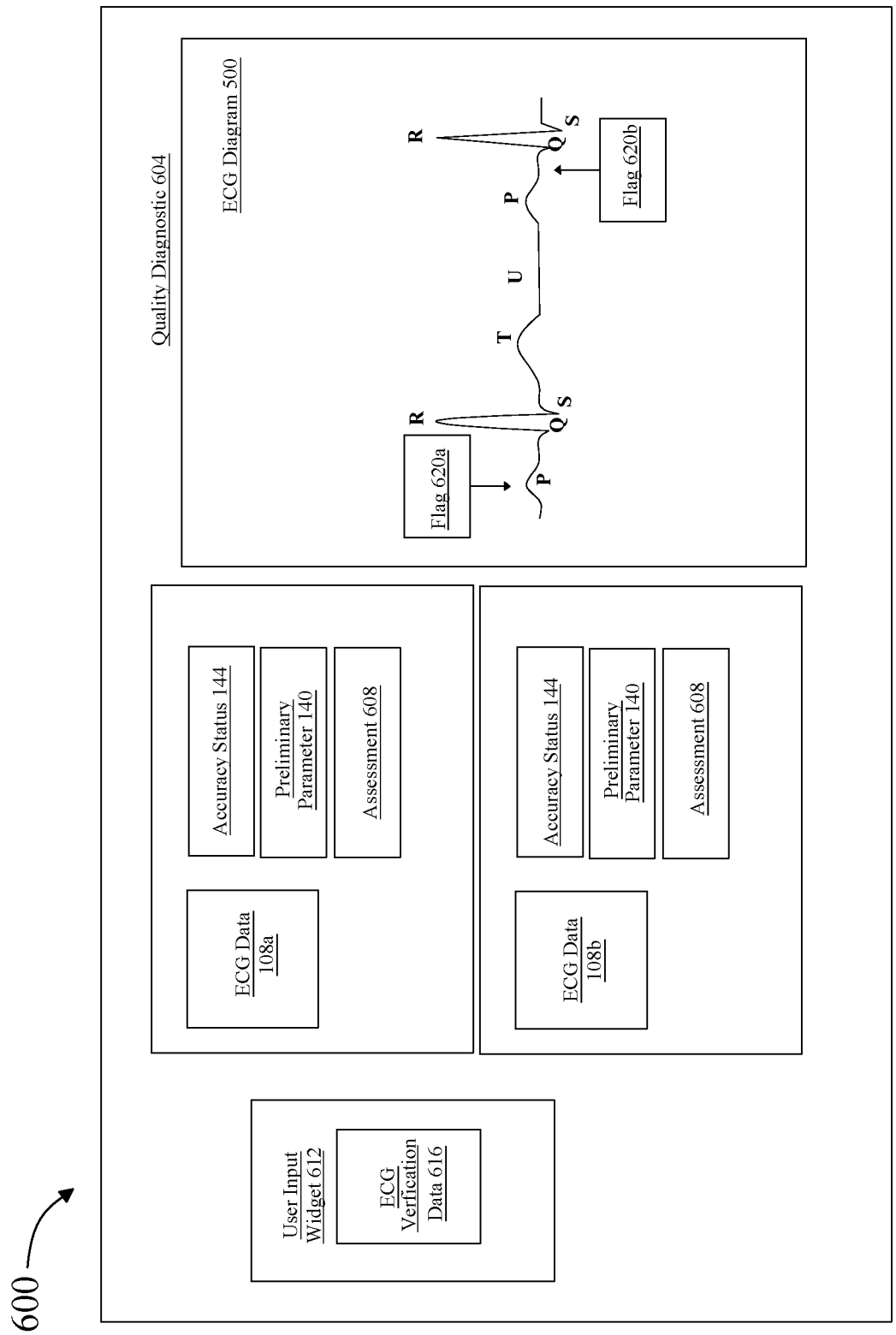
FIG. 6, is a diagram of a user interface for displaying a quality diagnostic.

Referring now to FIG. 6, an exemplary diagram of a user interface 600 for displaying a quality diagnostic 604. Quality diagnostic 604 may display ECG data 108 as extracted from the ECG printout 120 as described above. For example, quality diagnostic 604 may display ECG signals 112 and ECG parameters 116, ECG diagram 500, and the like. Quality diagnostic 604 may display a correlating accuracy status 144 and preliminary ECG parameters 140 next to validated or invalidated ECG signals 112 and ECG parameters 116. Displaying preliminary ECG parameters 140 may allow a user to visually see the derived parameters based on the calculations described above in comparing to ECG data 108. Additionally, an assessment 608 may be displayed wherein assessment 608 includes the analysis conducted in validating or invalidating ECG data 108, such as textbook validators as described above. Quality diagnostic 604 may display a user input widget 612 where a user may verify ECG data 108 by user input. The user input may include ECG verification data wherein a user may submit any data to verify or invalidate data presented in quality diagnostic 604. For example, the user input may include the threshold for the scoring algorithms, validation of ECG signals, feedback on textbook validators and the like. Quality diagnostic 604 may display flags 620 indicating an issue with ECG data 108 as described above. For example, flags 620 may mark/highlight sections or intervals of ECG diagram 500 indicating presence of noise and the like. Assessment 608 may include the descriptions of the flags 620 for user review.

Figure 7:
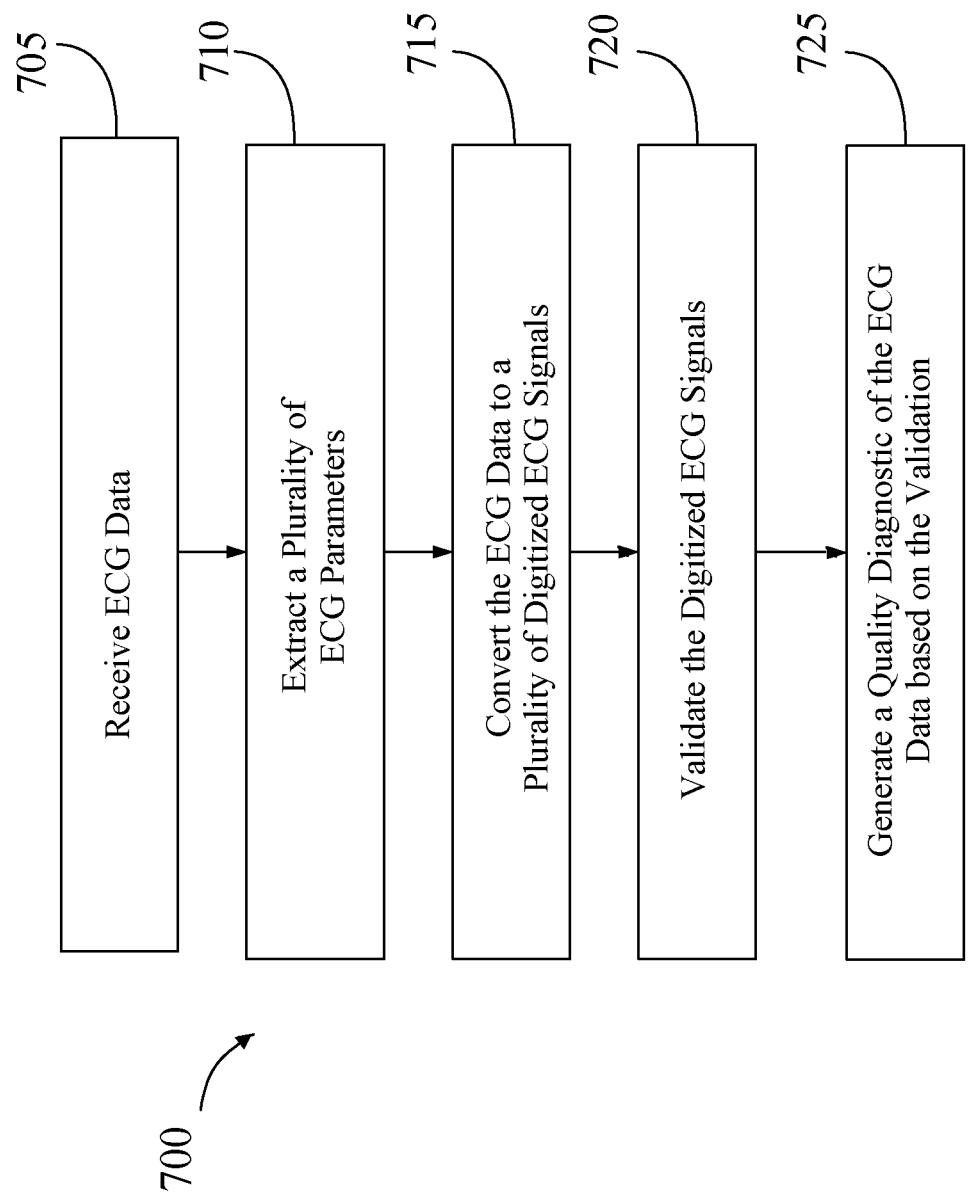
FIG. 7 is a block diagram of an exemplary embodiment of a method for a quality diagnostic of analog ECG (electrocardiogram) data.

Referring now to FIG. 7, an exemplary diagram of a method 700 for generating a quality diagnostic of ECG data is illustrated. This may be implemented as disclosed in and with reference to FIGS. 1-4. At step 705, method 700 includes receiving, by a computing device, ECG data. This may be implemented as disclosed in and with reference to FIGS. 1-4. At step 710, method 700 includes extracting, by the computing device, a plurality of ECG parameters from the ECG data. This may be implemented as disclosed in and with reference to FIGS. 1-4. At step 715, method 700 includes converting, by the computing device, the ECG data to a plurality of digitized ECG signals. This may be implemented as disclosed in and with reference to FIGS. 1-4. At step 720, method 700 includes validating, by the computing device, the digitized ECG signals, wherein validating comprises classifying the plurality of digitized ECG signals to a plurality of preliminary ECG parameters and determining an accuracy status of the extracted plurality of ECG parameters by comparing the plurality of preliminary ECG parameters to the extracted plurality of ECG parameters. At step 725, method 700 includes generating, by the computing device, a quality diagnostic of ECG data based on validation of the digitized ECG signals. This may be implemented as disclosed in and with reference to FIGS. 1-4.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
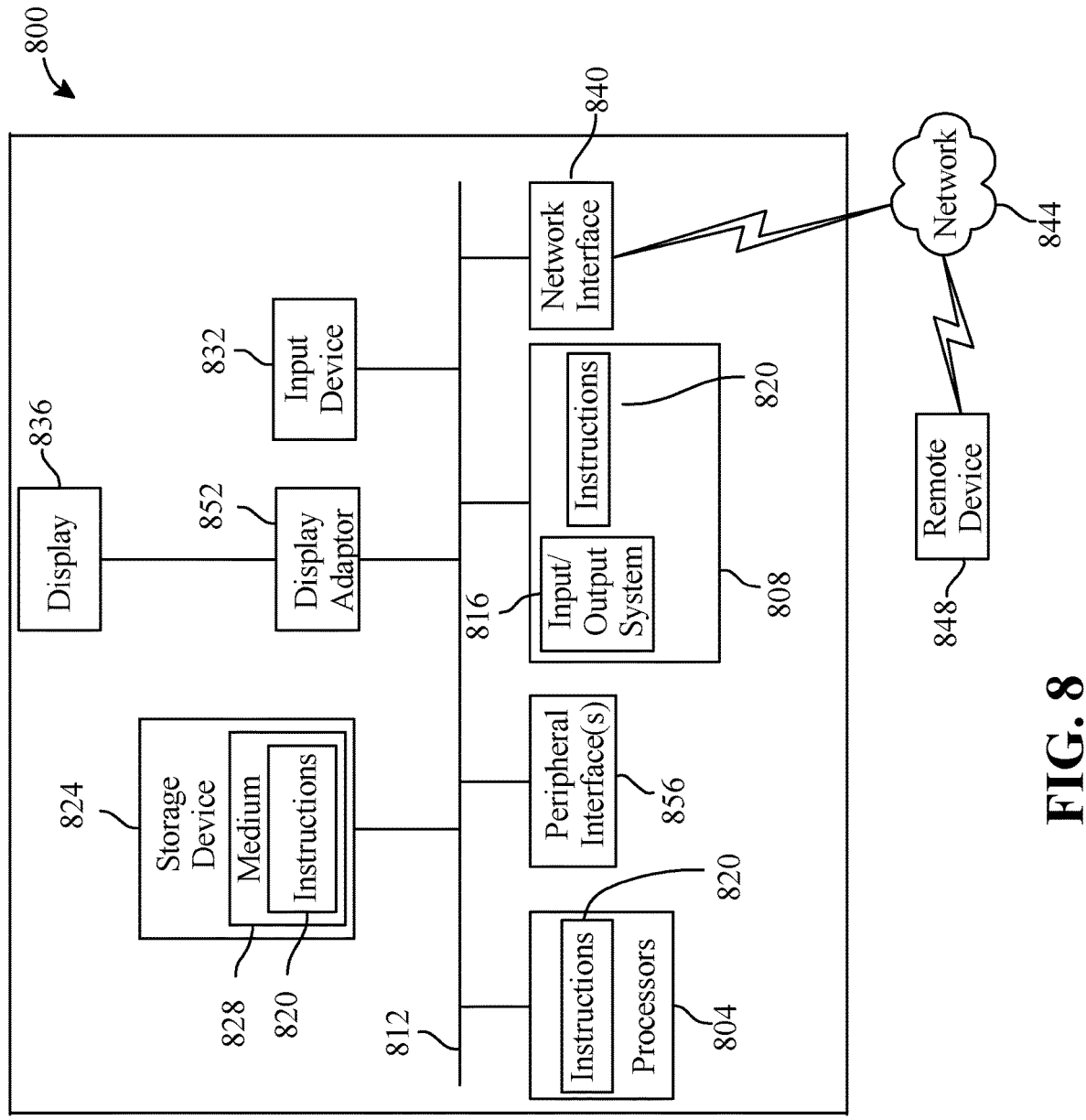
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for generating a quality diagnostic of analog ECG (electrocardiogram) data, wherein the apparatus comprises:

at least a processor; and a memory communicatively connected to the at least a processor, wherein the memory contains instructions configuring the at least a processor to:

receive an image of ECG data;

extract a plurality of ECG parameters from the image of ECG data;
convert the image of the ECG data to one or more digitized ECG signals;
validate the one or more digitized ECG signals, wherein validating comprises:
classifying the one or more digitized ECG signals to a plurality of preliminary ECG parameters; and
determining an accuracy status of the extracted plurality of ECG parameters by comparing the plurality of preliminary ECG parameters to the extracted plurality of ECG parameters, wherein:
the accuracy status further comprises a variable indicating accuracy of the plurality of preliminary ECG parameters;
determining an accuracy status comprises using a scoring algorithm using a threshold to determine the accuracy status, wherein the accuracy status comprises one of a pass status and a fail status, and wherein the apparatus is configured to generate the threshold by:
training a threshold classifier with training data correlating a plurality of annotations indicating abnormalities to a plurality of thresholds:
inputting the analog ECG data into the threshold classifier; and
outputting, by the threshold classifier, the threshold; and
generate a quality diagnostic of the image of ECG data based on validation of the one or more digitized ECG signals, wherein the quality diagnostic represents a degree of quality of the image of ECG data.

2. The apparatus of claim 1, wherein the ECG data comprises an ECG printout comprising one or more ECG signals and the plurality of ECG parameters.

3. The apparatus of claim 1, further comprising a machine vision system, wherein the memory contains instructions further configuring the at least a processor to:
capture the image of the ECG data; and
extract the plurality of ECG parameters from the image.

4. The apparatus of claim 3, wherein:
the machine vision system comprises an optical character recognition reader; and
the memory contains instructions further configuring the at least a processor to extract the plurality of ECG parameters from the image using the optical character recognition reader.

5. The apparatus of claim 1, wherein classifying the plurality of digitized ECG signals comprises:
training a validation classifier using training data comprising a plurality of digitized ECG signals correlated to a plurality of textbook validators of ECG parameters;
inputting the plurality of digitized ECG signals into the validation classifier; and
outputting, by the validation classifier, the plurality of preliminary ECG parameters.

6. The apparatus of claim 1, wherein determining an accuracy status comprises using a scoring algorithm using a threshold to determine the accuracy status, wherein the accuracy status comprises one of a pass status and a fail status.

7. The apparatus of claim 6, wherein the memory contains instructions further configuring the at least a processor to determine the threshold by:
training a threshold classifier with training data correlating a plurality of annotations indicating abnormalities to a plurality of thresholds;
inputting the analog ECG data into the threshold classifier; and
outputting, by the threshold classifier, the threshold.

8. The apparatus of claim 1, wherein the quality diagnostic comprises an auditory representation comprising sounds to indicate a pass status or a fail status regarding an overall quality of the analog ECG data.

9. The apparatus of claim 1, wherein generating the quality diagnostic comprises generating a visual representation regarding the quality status of the analog ECG data by:
training a diagnostic classifier with training data correlating analog ECG data to a plurality of flags;
inputting the analog ECG data into the diagnostic classifier; and
outputting, by the diagnostic classifier, one or more flags indicating an issue with the analog ECG data.

10. The apparatus of claim 1, wherein validating the digitized ECG signals comprises receiving ECG verification data from a user comprising a threshold for a scoring algorithm.

11. A method for generating a quality diagnostic of analog ECG (electrocardiogram) data, wherein the method comprises:
receiving, by at least a processor, an image of ECG data;
extracting, by the at least a processor, a plurality of ECG parameters from the image of ECG data;
converting, by the at least a processor, the image of ECG data to one or more digitized ECG signals;
validating, by the at least a processor, the digitized ECG signals, wherein validating comprises:
classifying, by the at least a processor, the plurality of digitized ECG signals to a plurality of preliminary ECG parameters; and
determining, by the at least a processor, an accuracy status of the extracted plurality of ECG parameters by comparing the plurality of preliminary ECG parameters to the extracted plurality of ECG parameters, wherein:
the accuracy status further comprises a variable indicating accuracy of the plurality of preliminary ECG parameters;
determining an accuracy status comprises using a scoring algorithm using a threshold to determine the accuracy status, wherein the accuracy status comprises one of a pass status and a fail status, and wherein generating the threshold further comprises:
training a threshold classifier with training data correlating a plurality of annotations indicating abnormalities to a plurality of thresholds:
inputting the analog ECG data into the threshold classifier; and
outputting, by the threshold classifier, the threshold; and
generating, by the at least a processor, a quality diagnostic of the image of ECG data based on validation of the digitized ECG signals, wherein the quality diagnostic represents a degree of quality of the image of ECG data.

12. The method of claim 11, wherein the ECG data comprises an ECG printout comprising one or more ECG signals and the plurality of ECG parameters.

13. The method of claim 11, wherein receiving the ECG data comprises:
capturing, using a machine vision system, the image of the ECG data; and extracting, using the machine vision system, the plurality of ECG parameters from the image.

14. The method of claim 13, wherein extracting, using the machine vision system, the plurality of ECG parameters further comprises using an using an optical character recognition reader.

15. The method of claim 11, wherein classifying the plurality of digitized ECG signals comprises:
- training a validation classifier using training data comprising a plurality of digitized ECG signals correlated to a plurality of textbook validators of ECG parameters;
- inputting the plurality of digitized ECG signals into the validation classifier; and
- outputting, by the validation classifier, the plurality of preliminary ECG parameters.

16. The method of claim 11, wherein determining an accuracy status comprises using a scoring algorithm using a threshold to determine the accuracy status, wherein the accuracy status comprises one of a pass status and a fail status.

17. The method of claim 16, wherein using the scoring algorithm comprises determining the threshold by:
- training a threshold classifier with training data correlating a plurality of annotations indicating abnormalities to a plurality of thresholds;
- inputting the analog ECG data into the threshold classifier; and
- outputting, by the threshold classifier, the threshold.

18. The method of claim 11, wherein the quality diagnostic comprises an auditory representation comprising sounds to indicate a pass status or a fail status regarding an overall quality of the analog ECG data.

19. The method of claim 11, wherein generating the quality diagnostic comprises generating a visual representation regarding the quality status of the analog ECG data by:
- training a diagnostic classifier with training data correlating analog ECG data to a plurality of flags;
- inputting the analog ECG data into the diagnostic classifier; and
- outputting, by the diagnostic classifier, one or more flags indicating an issue with the analog ECG data.

20. The method of claim 11, wherein validating the digitized ECG signals comprises receiving ECG verification data from user comprising a threshold for a scoring algorithm.

* * * * *